United States Patent [19]

Kay et al.

[11] Patent Number: 4,696,912

[45] Date of Patent: Sep. 29, 1987

[54] STABILIZED COMPOSITIONS

[75] Inventors: Allen I. Kay, Succasunna; Gerard C. Hokanson, Long Valley, both of N.J.

[73] Assignee: Warner-Lambert Company, Morris Plains, N.J.

[21] Appl. No.: 818,504

[22] Filed: Jan. 10, 1986

[51] Int. Cl.[4] ............................................ A61K 37/16
[52] U.S. Cl. ........................................................ 514/7
[58] Field of Search ............................................ 514/7

[56] References Cited

U.S. PATENT DOCUMENTS 4,578,383 3/1986 Stampwala et al. .................... 514/7

Primary Examiner—Jerome D. Goldberg
Attorney, Agent, or Firm—Ronald A. Daignault

[57] ABSTRACT

The antimicrobial agent CL-1565-A can be effectively stabilized for up to about two years using certain salts or esters of carboxylic acids or their precursors as stabilizing additives.

2 Claims, No Drawings

STABILIZED COMPOSITIONS

BACKGROUND

The antimicrobial agent known as CL-1565A has been shown to be useful as an antibiotic, e.g., against various micro-organisms and as an agent for treating cancer cells.

While the drug is highly useful it is nonetheless relatively unstable. For instance, it decomposes 31% in five weeks at 25° C. in the solid state and 48% in 23 days at a concentration of 15 mg/mL in aqueous solution.

RELATED APPLICATIONS

This application is related to U.S. Ser. No. 627,367 filed July 2, 1984, now U.S. Pat. No. 4,578,383.

THE INVENTION

The invention is directed to stabilized drug compositions based on the phosphorous-containing antibiotic known as CL1565-A and methods of making such compositions. The stabilized compositions contain CL1565-A and a salt of ascorbic acid.

CL1565-A is believed to have the structure:

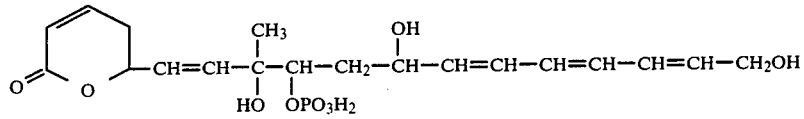

The compound is obtained via the fermentation of a strain of Streptomyces sp., isolate ATCC 31906. This invention covers compositions containing the complex shown above, as produced by the process disclosed infra, as well as congeners and pharmaceutically acceptable derivatives, eg; salts thereof.

In certain preferred embodiments, sodium ascorbate (pH 6.0-7.0 from NaOH and ascorbic acid) is added to solutions of CL-1565A to yield compositions showing molar ratios of 1:0.5 to 1:6 for CL-1565A to sodium ascorbate.

ADVANTAGES

The invention offers several advantages over known formulations containing antibiotic and antitumor agents. In addition to the therapeutic effectiveness of the active agent; i.e., CL-1565-A, the compositions of the invention are advantageous because they need not be stored under refrigeration for protracted periods.

Furthermore, stabilized solutions made in accordance herewith can be lyophilized to yield solid materials which can be readily handled and stored.

Other aspects and advantages of the invention will become apparent after a consideration of the following description.

DESCRIPTION OF THE INVENTION

The present invention relates to stable compositions comprising a phosphorus-containing antibiotic that is an antitumor agent, designated CL-1565-A, congeners, and pharmaceutically acceptable derivations, e.g., salts thereof, and to a process for the production and the method of using said compositions.

In addition, the invention relates to pharmaceutical compositions containing various forms of the compound of the invention alone or in combination with drugs and the use of same, with optional pharmaceutically acceptable carrier(s) in the treatment of neoplastic diseases and microbial disorders.

CL-1565-A: CULTURE CHARACTERIZATION AND FERMENTATION PROCESSES

In accordance with the present invention, CL-1565 compounds are produced by cultivating a selected CL-1565-complex producing strain of a Streptomyces sp., isolate ATCC 31906, under artificial conditions in a suitable nutrient medium until a substantial quantity of CL-1565 compound or compounds (especially CL-1565-A CL-1565-B and CL-1565-T) is formed and isolating one or more of the compounds in a suitable, e.g., salt, form.

The strain of Streotomyces suitable for the purpose of this invention was found in a soil sample collected in Sao paulo, Brazil. This organism was isolated from the soil sample using a suitable agar plating medium. An example of such a medium is one which contains salts such as potassium phosphate, magnesium sulfate, and ferrous sulfate, and carbon substrates such as glycerol and asparagine. The soil was pretreated with calcium carbonate before it was plated on the agar medium and incubated under a favorable temperature, particularly 24° C., to allow the development of the soil microorganisms.

The CL-1565-complex producing organism that was isolated is an unidentified strain of Streptomyces and has been deposited with the American Type Culture Collection, Rockville, Md. 20852, and is being maintained in their permanent culture collection as ATCC 31906. This organism that produces CL-1565-A and its congeners is maintained as a dormant culture in lyophile tubes, cryogenic vials, and in soil tubes at the Warner-Lambert/Parke-Davis Culture Laboratory and is designated as isolate WP-426.

The antitumor compound CL-1565-A and closely related congeners including CL-1565-B and CL-1565-T, are Produced by isolate WP-426 during aerobic fermentation under controlled conditions. The fermentation medium consists of sources of carbon, nitrogen minerals, and growth factors. Examples of carbon sources are various simple sugars such as cerelose, mannose, fructose, xylose, ribose, and glycerol, or other carbohydrate containing compounds such as dextrin, starch, corn meal, and whey. The normal quantity of the carbon sources varies from 0.1 to 10 percent by weight.

The nitrogen sources are organic, inorganic, or mixed organic-inorganic in nature. Examples of such compounds are cotton seed meal, soybean meal, corn germ flour, corn steep liquor, distillers solubles, peanut meal, peptonized milk, and various ammonium salts. The normal amounts are also acceptable.

The inclusion of minerals and growth factors in the fermentation medium is also helpful in the production of CL-1565-A and its congeners. Examples of media ingredients that provide minerals are potassium phosphate, sodium chloride, ferrous sulfate, calcium carbonate, cobalt chloride, and zinc sulfate. The sources of growth factors include various yeast and milk products The preferred method for producing CL-1565-A and its congeners is by submerged culture fermentation.

According to an embodiment of this invention, fermentation ingredients are prepared in solution and sterilized by autoclaving or steam heating. The pH of the aqueous medium is preferably between 4 and 8. The fermentation medium is cooled to a suitable temperature. between 16° and 45° C., and then inoculated with the suitable culture. Fermentation is carried out with aeration and agitation, and the maximum production of CL-1565-A and its congeners is usually reached in 2-10 days. Fermentation in solid state can also be used for the production of CL-1565-A and its congeners.

In the submerged culture method, fermentation is carried out in shake flask or in stationary tank fermentors. In shake flasks, aeration is brought about by agitation of the flasks which causes mixing of the medium with air. In the stationary fermentors, agitation is provided by impellers in the form of disc turbines, vaned discs, open turbines, or marine propellers. Aeration is accomplished by injecting air or oxygen into the fermentation mixture.

STABILIZING ADDITIVES

The additives used to stabilize CL-1565-A-based compositions in accordance with the invention are salts or esters of ascorbic acid. While metal salts are preferred, ammonium salts and other equivalent compounds are operable.

Preferred esters constitute ascorbic acid esterified with alcohols possessing substituted or unsubstituted alkyl groups. The alkyl groups will generally have from about one to about five carbon atoms. Highly preferred esters are the methyl and ethyl esters.

Preferred ascorbate salts to be used in the invention are alkali or alkaline earth metal salts of the acid. Salts of alkali metals, e.g., Na, K. and Li, are more preferred. Sodium salts are most preferred. Mixtures are contemplated.

Any functional eguivalent of the stabilizing additive can be used. Thus precursors—combinations or substances which yield the useful ascorbates upon contacting with the drug component—can be used.

The stabilizing additive of the invention may be used in combination with various conventional additives, e.g., other stabilizers, excipients, and the like, so long as the presence of such additives is not deleterious to the effectiveness of the drug, the stabilizer, or the final preparation.

THE COMPOSITIONS

The stabilized compositions produced in accordance herewith are made by combining the one or more stabilizing additives with one or more of CL-1565A and its functionally equivalent form(s) under suitable conditions.

The compositions of the invention will contain final quantities of CL-1565-A and stabilizer such that their molar ratios will be from about 1:0.5 to about 1:6 for drug to stabilizer. Preferably, the ratios will be about 1:1 to about 1:4 (CL-1565-A to stabilizer).

While the order of addition is not deemed critical, it is generally preferred that the stabilizing additive be added to a suspension or solution of the drug.

The form of CL-1565-A which is used is not critical. Thus, prior to use of the stabilizer, the drug may be wholly or partially reacted with cations such as ammonium groups, quaternary ammonium salt groups, sodium ions, calcium ions, potassium ions and the like.

The addition of one or more conventional pharmaceutical ingredients, e.g., water, colorants, perfumes, solid diluents (e.g., bulking agents) and the like, can be carried out before, during, or after the mixing of the drug and stabilizers.

Following the preparation of the stabilized compositions, conventional processing techniques, such as lyophilization, can be employed to put the composition into solid cake form or other forms suitable for handling and/or storage.

Once stabilized, the antibiotic CL-1565-A and/or its congeners can be used for their antimicrobial and antitumor activity in the form of pharmaceutical compositions containing any of the various metallic salts such as the sodium, potassium, magnesium, calcium, barium, aluminum, zinc or iron salt, and the like, or as other salts such as the ammonium salt or salts formed from suitable organic amines. Such pharmaceutical compositions are used with a compatible pharmaceutically acceptable carrier. The compositions may also contain other active antimicrobial and/or antitumor agents.

The compositions may be made up in any pharmaceutical form appropriate for the route of administration in question. Examples of such compositions are well known to practitioners of the pharmaceutical art and include solid compositions for oral administration such as tablets, capsules, pills, powders and granules, liquid compositions for topical or oral administration such as solutions, suspensions, syrups and elixirs, and preparations for parenteral administration such as sterile solutions, suspensions, or emulsions.

For use as a therapeutic agent, the compositions are often administered so that the concentration of active ingredient is greater than the minimum inhibitory concentration for the particular organism or condition being treated.

EXAMPLES

The examples which follow illustrate the preferred methods by which CL-1565-A, its congeners and the compositions of the invention are produced. The described compositions and processes are capable of wide variation, and any minor departure or extension is considered as within the scope of this invention.

Examples 1-10 demonstrate the preparation and use of CL-1565-A and some of its derivatives.

Examples 11-13 show the preparation of the compositions of the invention and their superior stability when compared to unstabilized drug preparations.

EXAMPLE 1

Seed development and shake flask fermentation

The culture in its dormant stage is transferred to a CIM-23 agar slant and incubated for 7-14 days at 28° C. A portion of the microbial growth from the slant is used to inoculate an 18×150 mm seed tube containing 5 ml of ARM 1550 seed medium. The seed tube is shaken at 24° C. for 3-4 days.

| CIM 23 agar slant | |
|---|---|
| Amidex corn starch | 10 g |
| N-Z amine, type A | 2 g |
| Beef Extract (Difco) | 1 g |
| Yeast Extract (Difco) | 1 g |

| -continued | |
|---|---|
| Cobaltous chloride 6 H₂O | 0.020 g |
| Agar | 20 g |
| Distilled water | 1000 ml |

| ARM 1550 medium | % |
|---|---|
| Bacto-Yeast Extract (Difco) | 0.5 |
| Glucose,Monohydrate | 0.1 |
| Soluble Starch (Difco) | 2.4 |
| Bacto-Tryptone (Difco) | 0.5 |
| Bacto-Beef Extract (Difco) | 0.5 |
| CaCO₃ | 0.2 |

Note: Adjust pH to 7.5 with NaOH before adding CaCO₃

A portion (1 ml) of the microbial growth from the seed tube is transferred to a 300 ml Erlenmeyer baffled shake flask containing 50 ml of SM 64 production medium. The inoculated flask is incubated at 24° C. for 5 days with shaking using a gyratory shaker (2" throw) set at 180 RPM. The fermentation beer after five days of fermentation is tan in color, the mycelia are granular in appearance, and the PH of the fermentation beer is about 5.5.

| SM 64 Production Medium | |
|---|---|
| Whey (Kroger Dairy) | 35.0% by volume |
| Dextrin (Amidex B411), American Maize | 1.5% by weight |
| Pharmamedia (Traders Protein 431307 | 1.5% by weight |
| Distilled water | |

Note: Adjust pH to 6.5 with sodium hydroxide

The fermentation broth containing CL-1565-A and its congeners is assayed at a 1:100 dilution vs. L1210 mouse leukemia cells in vitro. A 0–50% growth of cells compared with an L1210 cell control is considered to indicate activity, with 0% being the most active. The cytotoxicity of two experimental shake flask fermentations were:

| | Cytotoxicity (% Growth) | |
|---|---|---|
| Flask Number | Supernatant | Freeze-dried |
| I. | 28 | 14 |
| II. | 17 | 30 |

The above fermentation broths were also tested vs. several microorganisms using the agar-disc method. The crude broth was found to be active vs. *Neisseria catarrhalis* 03596, *Staphylococcus aureus* 02482, *Bacillus subtilis* 04555, *Kloeckera brevis* M1378, *Rhodotorula glutinis* M1384, *Saccharomyces cerevisiae* 01525 and *Penicillium avellaneum* M2988.

EXAMPLE 2

Fermentation in 200-gallon fermentors

Seed Development

A cryogenic vial containing approximately 1 ml of culture suspension is used as the source of inoculum. The contents of this cryogenic vial are thawed and aseptically transferred to a two liter, baffled Erlenmeyer flask containing 500 ml of SD-05 seed medium. The inoculated flask is incubated for 46–48 hours at 24° C., on a gyratory shaker, at 130 rpm speed.

| SD-05 Seed Medium | % |
|---|---|
| Amberex 1003 (Amer Labs) | 0.5 |
| Glucose Monohydrate (Cerelose) | 0.1% |
| Dextrin-Amidex B411 (Corn Products) | 2.4 |
| N-Z Case (Humko Sheffield) | 0.5 |
| Spray Dried Meat Solubles (Daylin Labs) | 0.3 |
| CaCO₃ | 0.2 |
| Distilled Water | |

After 48 hours, the contents of the seed flask are transferred aseptically to a 30-liter, stainless steel fermentor containing 16 liters of SD-05 seed medium. The inoculated fermentor is incubated for 18–24 hours at 24° C., stirred at 300 RPM, and sparged with air at 1 VVM rate. This microbial growth is used to inoculate the 200-gallon production fermentor.

Production Fermentors

A 200-gal fermentor which contains 160 gal of SM 64 production medium is sterilized by heating with steam for 40 min. at 121° C. The medium is cooled to 24° C. and then inoculated with about 16 liters of the microbial growth from the 30-liter seed fermentor. The inoculated medium is allowed to ferment for 5–7 days at 24° C., 190 RPM agitation, and sparged with 1 VVM air. Antifoam agents, Dow Corning "C" and polyglycol P-2000, are used to control foaming.

The production of CL-1565-A and at least two related antitumor antibiotics; namely. CL-1565-B and CL 1565-T, are monitored throughout the fermentation cycle by recording fermentation parameters such as pH and percent sedimentation or growth as well as by in vitro assays vs. L1210 mouse leukemia cells and a high pressure liquid chromatographic procedure described later. An example of a fermentation profile in a 200-gal fermentor is shown in the following table.

| Fermentation Time (hr) | pH | % Sedimentation (growth) | % Growth of L1210 Cells | | | Micrograms CL-1565-A/ml (HPLC Assay) |
|---|---|---|---|---|---|---|
| | | | 1:100 | 1:300 | 1:1000 | |
| 0 | 6.0 | 0 | — | — | — | — |
| 12 | 5.8 | 3.6 | — | — | — | — |
| 24 | 5.1 | 13.3 | NA* | — | — | — |
| 36 | 5.15 | 14.7 | NA | — | — | — |
| 48 | 5.35 | 19.3 | NA | NA | NA | — |
| 72 | 5.45 | 22.0 | NA | NA | NA | 3–6 |
| 96 | 5.95 | 24.7 | 18.2 | 52.9 | NA | 10–20 |
| 118 | 7.65 | 43.3 | 0 | 30.2 | NA | 50–65 |
| 132 | 7.80 | 39.3 | 0 | 23.9 | NA | 60–65 |
| 142 | 7.90 | 40.0 | 0 | 17.2 | NA | 60–70 |

NA* = not active

This fermentor was harvested after 142 hours of fermentation with a harvest volume of 140 gal.

EXAMPLE 3

Isolation of CL-1565-A

The harvested beer from the above fermentation was mixed with 34 kg of Celite 545 and filtered through a plate and frame filter press. The filtrate (473 liters) was percolated through a 30.5 cm [O.D.] column containing liters of HP-20 resin (Gillies International, Inc. La Jolla , Calif. The resin was then washed with water (605 liters), and 90:10 water:methanol (170 liters). Most of the CL-1565-A was then eluted from the resin with 80:20 water:methanol. High pressure liquid chromatographic analyses (HPLC), performed in the manner described below, of the ensuing eluates showed the following elution profile.

| 80:20 water:methanol eluate | grams of CL-1565-A |
|---|---|
| #1 = 340 liters | <2 g |
| #2 = 340 liters | 11.5 g |
| #3 = 340 liters | 7.0 g |

Eluates #2 and #3 were separately concentrated and lyophilized to afford 90.2 g and 78.7 g, respectively, of dark brown solids. These products were combined and dissolved in 3 liters of water. The resulting solution was added to 27 liters of methanol with stirring. After standing overnight at 5° C., the mixture was filtered and the precipitate was washed with 5 liters of methanol. The filtrate and wash were combined, concentrated in vacuo, and lyophilized to yield 104.5 g of a solid. A portion of this product (95 grams) in 1.5 liters of water was added slowly with mixing to 17 liters of 1-propanol. After one hour the resulting mixture was filtered and the precipitate was washed with 2 liters of 1-propanol. The filtrate and wash were combined, concentrated, and lyophilized to afford 57 g of a solid which, by HPLC analysis, contained about 15 g of CL-1565-A.

This product was chromatographed, in approximately 15 g lots, on 1.2 liters of 40 um $C_{18}$-silica gel (Analytichem International, Inc., Harbor City, Calif.) contained in a 7.6 cm [O.D.] column. The eluent used was 0.005 M pH 4.5 ammonium acetate buffer followed by 0.005 M PH 4.5 ammonium acetate containing 5% acetonitrile. The fractions collected were assayed by HPLC. The fractions containing CL 1565-A were pooled, concentrated, and lyophilized. A portion (570 mg) of the resulting product was rechromatographed using a prep LC/System 500 apparatus fitted with a prep-pak TM -500/$C_{18}$ column (Waters Instruments, Inc., Milford, Mass.) and 0.1 M pH 6.5 phosphate buffer containing 10% acetonitrile as the eluent. The major fractions, containing approximately 375 mg of CL-1565-A, Were pooled and concentrated in vacuo. The aqueous solution was passed through a column containing 200 ml of HP-20 resin packed in water. The resin was then washed with 1400 ml of water and CL-1565-A remaining on the column was eluted with 350 ml of 50% methanol.

EXAMPLE 4

The eluate from the final HP-20 resin column of Example 3, containing CL-1565-A, was concentrated in vacuo and passed through a column containing 35 ml of Dowex-50X2 ion exchange resin in the $Na^+$ form. The effluent (PH 5.5) was combined with a water wash of the ion exchange resin column and lyophilized to yield 180 mg of purified CL-1565-A as the sodium salt. Analysis of this material showed that it contained approximately 1.3 moles of sodium per mole of the parent CL-1565-A acid.

Addition of a small amount, e.g., a trace, of acid such as hydrochloric, sulfuric, or phosphoric acid, to the solution of the monosodium salt of CL-1565-A produces the acid form.

The free acid forms of the compounds are somewhat unstable and it is preferred that CL-1565-A, CL-1565-B, and CL-1565-T be isolated as their ammonium salts or as salts of a pharmaceutically acceptable metal or amine cation. Suitable pharmaceutically acceptable salts of CL-1565-A, CL-1565-B, and CL-1565-T include the ammonium salt and salts of metals including sodium, potassium, magnesium, calcium, barium, aluminum, zinc, iron and the like. Pharmaceutically acceptable salts of the compounds are also formed from pharmaceutically acceptable organic amine cations.

The term "pharmaceutically acceptable amine cation" contemplates the positively charged ammonium ion and analogous ions derived from organic nitrogenous bases strong enough to form such cations. Bases useful for the purpose of forming pharmacologically-acceptable nontoxic salts of such compounds containing free phosphate groups form a class whose limits are readily understood by those skilled in the art.

As illustrated in Examples 5 and 6, various salts of CL-1565-A, CL-1565-B, and CL-1565-T are prepared from the sodium salt by passing a solution of the sodium salt through an ion exchange column which has been previously loaded with the desired ion. For example, salts with inorganic bases, alkali metal salts, alkaline earth metal salts or salts with other inorganic cations are prepared by passing an aqueous solution of one a suitable reagent, such as the sodium salt, through an ion exchange column such as Dowex-50X1 or Dowex-50X2 which has been previously converted to the desired salt form by passage of a solution of the chloride salt of the desired metal or other cation. Correspondingly, the ammonium salt or organic amine cation salts are prepared in a similar fashion. The ion exchange column is converted to the desired cationic form by passage of ammonium chloride or the chloride salt of the desired organic amine cation through the column. The sodium ion form of CL-1565-A, CL-1565-B, or CL-1565-T is then passed through the column to obtain the desired salt.

The salts of the compounds in accordance with the present invention prepared by either method detailed above contain from about 1.0 to about 2.0 equivalents of cation per equivalent of the parent free acid. By the term "salt" of CL-1565-A, CL-1565-B or CL-1565-T is meant to include compounds in which the phosphate moiety is ionized and forms ionic salts with one to two molar equivalents of a monovalent cation, such as sodium ion, per molar equivalent of parent free acid, as well as compounds having from about one-half to one molar equivalent of a divalent cation, such as calcium ion, per molar equivalent of the parent free acid.

EXAMPLE 5

A column containing 50 ml of Dowex-50X1 resin in the ammonium ion form was converted to the calcium ion form by passing 200 ml of 0.7 M $CaCl_2$ through the column, followed by a water wash of 500 ml.

A solution of 50 mg of the sodium salt form of CL-1565-A contained in 15 ml of water was then passed through the column. Elution with water followed by lyophilization of the eluate yielded the calcium salt form of CL-1565-A. (%Na=0.00.)

EXAMPLE 6

A column containing 50 ml of Dowex-50X1 resin in the ammonium ion form was converted to the barium ion form by passing 200 ml of 1.0 M $BaCl_2$ through the column, followed by a water wash of 500 ml.

A solution of 50 mg of the sodium salt form of CL-1565-A contained in 15 ml of water was then passed through the column. Elution with water followed by lyophilization of the eluate yielded the barium salt form of CL-1565-A. (%Na=0.00.)

EXAMPLE 7

Filtered beer (719 liters), prepared in the same manner as described above, was passed over 31 liters of Dowex-1 x 2 (chloride form) packed in a 30.5 cm [O.D.] column. The effluent and the subsequent water wash did not contain any detectable amounts of the CL-1565 components as determined by using the HPLC method described below using 0.1M PH phosphate buffer (Na+)-acetonitrile (88:12) as the solvent system. The Dowex-1 resin was then eluted with 1M sodium chloride-methanol (1:1) and the eluate was collected in two 10-liter and six 15-liter fractions. Most of the CL-1565-A, CL-1565-B, CL-1565-T, and additional minor CL-1565 components appeared in eluates two through six. These fractions were combined and diluted with 246 liters of acetone. The resulting mixture was stored at 5° C. overnight. The clear supernatant solution was removed and concentrated to 16 liters in vacuo. Lyophilization of this solution yielded 740 g of product which was added to 552 g of a similar product isolated in the same manner and the combined solids were dissolved in 20 liters of water. The resulting solution (pH 6.0) was chromatographed over 50 liters of HP-20 resin contained in a 15 cm [O.D.] column. Elution of the HP-20 column with 175 liters of water removed most of the CL-1565-T and minor, more polar Cl-1565 components. Most of the CL-1565-A component was eluted with 100 liters of methanol-water (15:85); CL-1565-B and the remaining amount of CL-1565-A were eluted with 83 liters of methanol-water (50:50). The eluates richest in CL-1565-A were combined, concentrated, and lyophilized to afford 123 g of a solid which, by HPLC analysis, contained about 110 g of CL 1565-A.

A 75-gram portion of this product was dissolved in two liters of 0.05 M pH 6.8 phosphate buffer and further purified by chromatography over 52 liters (25 kg) of 100 um $C_{18}$ reverse phase silica gel (Analytichem International, Inc., Harbor City, Calif., packed in 0.05 M pH 6.8 phosphate buffer (Na+) in a 15 cm [O.D.] column. The column was developed with (0.05 M phosphate buffer containing increasing amounts (4.0-6.5%) of acetonitrile. The early fractions contained primarily CL-1565-T and additional minor, more polar CL-1565 components. The majority of the CL-1565-A component was eluted in subsequent fractions. The fractions containing CL-1565-A as the only UV-absorbing component were pooled and concentrated in vacuo to 20 liters. This concentrate was stored overnight at 5° C. and the inorganic salt that precipitated was filtered off. The filtrate was then charged on a 15 cm [O.D.] column containing 28 liters of HP-20 resin. The resin was washed with water (66 liters) and CL-1565-A was then eluted with 42 liters of methanolwater (50:50). The eluates that contained the majority of the CL-1565-A were combined (26 liters), concentrated, and lyophilized to yield 34 g of CL-1565-A containing some inorganic impurities. The inorganic impurities can be removed by dissolving the product in methanol (at 50 to 100 mg/ml, filtering off any insoluble material, and converting the filtrate to an aqueous solution by continually adding water to the filtrate as it is being concentrated in vacuo. Final purification of CL-1565-A is effected by chromatography of the resulting aqueous concentrate on HP-20 resin.

PROPERTIES OF CL-1565-A, SODIUM SALT

Ultraviolet Absorption Spectrum in MeOH: λmax 268 nm (a=805) with inflections at 259 and 278 nm.

Infrared Absorption Spectrum in KBr: Principal absorptions at: 3400, 1710, 1630, 1420, 1387, 1260, 1155, 1090, 1060, 975, 920, 820, and 775 reciprocal centimeters.

Optical Rotation: $[\alpha]+28.2°$ (1.0% in 0.1 M pH 7 phosphate buffer).

Elemental Analysis:

|  | % C | % H | % Na | % P |
|---|---|---|---|---|
| Calcd. for $C_{19}H_{27.7}O_{10}Na_{1.3}P$: | 47.84 | 5.86 | 6.27 | 6.49 |
| Found: | 48.01 | 5.88 | 6.05 | 6.3 |

Mass Spectrum (via fast atom bombardment):

| Calcd. for | $[C_{19}H_{25}Na_2O_9P+H]^+ =$ | m/z 475 |
|---|---|---|
|  | $[C_{19}H_{26}Na O_9P+H]^+ =$ | m/z 475 |
| Found: |  | m/z 425, 453 |

300 MHz Proton Magnetic Resonance Spectrum in $D_2O$: Principal signals at: (s=singlet, d=doublet, t=triplet, m=multiplet) 1.29 s (3H), 1.58 t (1H), 1.70 m (1H), 5.09 m (1H), 5.53 t (1H), 5.9–6.0 m (4H), 6.14 t (1H), 6.32 t (1H), 6.55 t (1H), 6.75 dd (1H), and 7.09 m (1H) parts per million downfield from tetramethylsilane (TMS).

$^{13}$C-Nuclear Magnetic Resonance Spectrum in $D_2O$: Principal signals at:

| peak number | | |
|---|---|---|
| 1 | 168.4 | |
| 2 | 149.8 | |
| 3 | 138.1 | |
| 4 | 135.0 | |
| 5 | 134.4 | |
| 6 | 131.2 | |
| 7 | 127.4 | |
| 8 | 126.7 | |
| 9 | 124.9 | |
| 10 | 124.8 | |
| 11 | 120.1 | |
| 12 | 79.5 | |
| 13 | 79.0 | |
| 14 | 75.6 | |
| 15 | 64.4 | |
| 16 | 62.7 | |
| 17 | 39.4 | |
| 18 | 29.7 | |
| 19 | 23.5 | parts per million downfield from tetramethylsilane (TMS). |

The $^{31}$p-Nuclear Magnetic Resonance Spectrum in $D_2O$ exhibits a doublet (J=10 Hz) at 0.504 ppm downfield from 85% phosphoric acid.

High Pressure Liquid Chromatography

Column: u Bondapak ™ $C_{18}$ silica gel (3.9 mm I.D. ×30 cm).

Solvent: 0.005M pH 7.3 sodium phosphate buffer-acetonitrile (90:10).

Flowrate: 2 ml/min.

Detection: ultraviolet absorption at 254 nm.

Retention time: 5.8 min

ANTIFUNGAL ACTIVITY

Paper disks (12.7 mm in diameter) impregnated with an aqueous solution containing 500 ug of CL-1565-A/ml were placed on a layer of agar inoculated with the indicated microorganisms. After incubation overnight at 28° C., the following zones of inhibition were observed.

| Organism | Zone diameter |
|---|---|
| *Saccharomyces cervisiae* | 25 mm |
| *Saccharomyces italicus* | 17 mm |
| *Saccharomycoides ludwigii* | 25 mm |

In Vitro Activity of CL-1565-A Against L1210 Leukemia Cells $ID_{50} = 0.078$ ug/ml In Vivo Antitumor Activity of CL-1565-A Against P388 Lymphatic Leukemia in Mice

| Dose | T/C* × 100 | | |
|---|---|---|---|
| (mg/kg/day) | test-1 | test-2 | test-3 |
| 25 | — | — | 174 |
| 17 | 256 | 248 | — |
| 12.5 | — | — | 150 |
| 8.5 | 256 | 209 | — |
| 6.3 | — | — | 142 |
| 4.3 | 170 | 172 | — |
| 2.1 | 173 | 157 | — |
| 1.1 | 170 | 139 | — |

*T/C = $\frac{\text{median survival time of treated mice}}{\text{median survival time of control mice}}$ The test method used is based on that described in *Cancer Chemother. Reports* 3:1-87 (part 3). 1972.

The examples which follow illustrate preferred pharmaceutical compositions containing one or more of the products, CL-1565-A, CL-1565-B, and CL-1565-T, for treatment of diseases, especially neoplastic diseases.

EXAMPLE 8

For parenteral use, a sterile, lyophilized product containing in each ampoule 75 mg of CL-1565-A, sodium salt is prepared from the solution of the compound (in injectable distilled water).

EXAMPLE 9

CL-1565-A, sodium salt: 7.5 mg
Sodium ascorbate: 33 mg

The above components are mixed in solution and a sterile, lyophilized product prepared. Solutions for injection are prepared by dissolving the above mixture in a physiological saline solution according to customary procedures. A buffering agent could be added according to need.

EXAMPLE 10

CL-1565-A sodium salt (1000 mg) and sodium ascorbate (440 mg) are dissolved in 100 ml of water. The solution is filtered through a sterile filter and aseptically filled into presterilized vials and lyophilized. The vials are sealed under nitrogen with presterilized closures and stored at 5° C. or lower.

For each of CL-1565-A, and its congeners, a suggested dosage regimen for use as an antitumor agent in mammalian species is 1.0–100 mg per square meter for a single daily intravenous treatment course.

EXAMPLE 11

An aqueous solution of CL-1565-A was prepared by dissolving 225 mg of CL-1565-A sodium salt ($C_{19}H_{25.5}O_9PNa_{1.5} \cdot 1.5 H_2O$, formula weight 490) in 30 ml of water. Sodium ascorbate (89.4 mg) was then added with stirring to obtain a final solution containing equimolar concentrations of CL-1565-A and sodium ascorbate. Aliquots (2 ml) of this solution were transferred to 6-ml serum vials and the water was removed by lyophilization.

EXAMPLE 12

An aqueous solution of ascorbic acid (MW 176) at a concentration of 19.5 mg/ml (0.11 mmole/ml) was prepared and the pH adjusted to 6.9 to 7.1 with 1 N sodium hydroxide solution. To this solution CL-1565-A is added with stirring to achieve a final concentration of 12.5 mg/ml [0.028 mmole/ml, based upon the anhydrous monosodium salt ($C_{19}H_{26}O_9PNa$, MW 452)]. Aliquots (2 ml) of this solution are transferred to 6-ml serum vials and the water is removed by lyophilization. Each of the resulting vials contains a mixture of sodium ascorbate (43.8 mg) and CL-1565-A (25 mg) in a molar ratio of 4 to 1.

EXAMPLE 13

The stability of aqueous solutions of CL-1565-A is given in Tables 1 and 2. Similar data for the solid form is in Table 3. Data for aqueous solutions is in Table 4.

TABLE 1

Stability of CL-1563-A in Solid State Form

| | % CL-1565-A Remaining After: | | |
|---|---|---|---|
| Storage Temperature | 1 Week | 3 Weeks | 5 Weeks |
| −15° C. | 100 | 100 | 100 |
| 5° C. | 100 | 100 | 100 |
| 25° C. | 87 | 77 | 69 |
| 37° C. | 70 | 26 | — |

*Samples prepared by lyophilization of 1.5 mL aliquots of an aqueous solution containing 15 mg of CL-1565-A per ml.

TABLE 2

Stability of CL-1565-A in Aqueous Solution

| | | % CL-1565-A Remaining After: | | |
|---|---|---|---|---|
| Concentration | Temp. | 7 Days | 14 Days | 23 Days |
| 5 mg/mL | 5° C. | 92 | 83 | 76 |
| | 25° C. | 77 | 63 | 45 |
| 15 mg/mL | 5° C. | 81 | 76 | 66 |
| | 25° C. | 67 | 55 | 42 |
| | 37° C. | 35 | — | — |

TABLE 3

Stability of CL-1565-A in Solid Form[a]

| | | % CL-1565-A Remaining After: | | | |
|---|---|---|---|---|---|
| Sample | Temp. | 3 Months | 5 Months | 9 Months | 23 Months |
| CL-1565-A Alone | −15° | 100 | 100 | 100 | 100 |
| | 5° | 88 | 86 | 79 | 74 |
| | 25° | 61 | — | — | — |
| CL-1565-A Plus | 5° | 100 | 100 | 100 | 100 |
| | 25° | 92 | 87 | 84 | 72 |

TABLE 3-continued

Stability of CL-1565-A in Solid Form[a]

| Sample | Temp. | % CL-1565-A Remaining After: | | | |
|---|---|---|---|---|---|
| | | 3 Months | 5 Months | 9 Months | 23 Months |
| Ascorbate[b] | | | | | |

[a]Samples prepared by lyophilization of 1.5 mL of an aqueous solution containing 15 mg/mL of CL-1565-A in 6-mL serum vials.
[b]Samples prepared by mixing CL-1565-A and sodium ascorbate (1:1 molar ratio) in solution prior to lyophilization.

TABLE 4

Stability of CL-1565-A in Aqueous Solution[a]

| Sample | Temp. | % CL-1565-A Remaining After | | |
|---|---|---|---|---|
| | | 2 Days | 23 Days | 54 Days |
| CL-1565-A Alone | 5° C. | 90 | 66 | — |
| | 25°C. | 87 | 42 | — |
| CL-1565-A Plus Ascorbate[b] | 5° C. | 100 | 94 | 88 |
| | 25° C. | 95 | 69 | 43 |

[a]Aqueous solutions containing 15 mg/mL of CL-1565-A.
[b]Solutions prepared by adding sodium ascorbate to solutions of CL-1565-A to yield an equimolar concentration.

The assay procedure used to generate the data shown in all of the tables was as follows:

CL-1565-A content was assayed by HPLC using a uBondapak C-18 silica gel column (Waters Assoc.) and 0.05 M pH 6.8 sodium phosphate buffer—acetonitrile (89:11) as the mobile phase, at a flow rate of 2 mL/minute. The retention time of CL-1565-A in this system is approximately 4.7 minutes. Solid samples were reconstituted in 100 mL of water immediately prior to HPLC assay. Solutions of CL-1565-A were diluted to a final concentration of 300 ug/mL with water prior to assay.

Reasonable variations, such as would occur to a skilled artisan, can be made herein without departing from the scope of the invention.

What is claimed is:

1. A stabilized drug composition containing
   (a) the compound of the formula

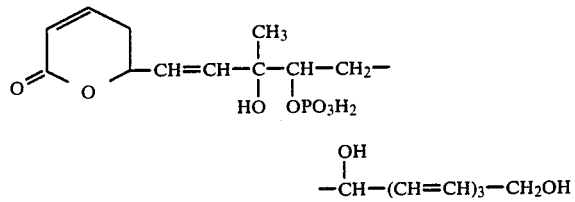

or a pharmaceutically acceptable salt thereof, and
   (b) a pharmaceutically acceptable alkali or alkaline earth metal salt or an alkyl ester of ascorbic acid in which alkyl group has one to five carbon atoms, wherein the molar ratio of (a) to (b) is from about 1:0.5 to about 1:6.

2. The composition of claim 1 wherein (b) is sodium ascorbate.

* * * * *